(12) United States Patent
Opolski et al.

(10) Patent No.: US 7,344,553 B2
(45) Date of Patent: Mar. 18, 2008

(54) COUPLING SYSTEM USEFUL IN PLACEMENT OF IMPLANTS

(75) Inventors: Steven W. Opolski, Carlisle, MA (US); Todd A. Peavey, Cambridge, MA (US)

(73) Assignee: NMT Medical, Inc., Boston, MA (US)

( * ) Notice: Subject to any disclaimer, the term of this patent is extended or adjusted under 35 U.S.C. 154(b) by 612 days.

(21) Appl. No.: 10/389,471

(22) Filed: Mar. 14, 2003

(65) Prior Publication Data
US 2003/0181945 A1    Sep. 25, 2003

Related U.S. Application Data

(60) Provisional application No. 60/382,528, filed on May 21, 2002, provisional application No. 60/364,017, filed on Mar. 15, 2002.

(51) Int. Cl.
A61B 17/28    (2006.01)
A61B 17/42    (2006.01)
A61B 17/44    (2006.01)

(52) U.S. Cl. ........................ 606/207; 606/205

(58) Field of Classification Search ........ 606/205–207, 606/142, 147, 106, 564, 104, 198; 600/564, 600/567; 24/598.5; 623/1.11
See application file for complete search history.

(56) References Cited

U.S. PATENT DOCUMENTS

| 430,849 | A | | 6/1890 | Groth |
| 1,299,821 | A | | 4/1919 | Carpmill et al. |
| 1,684,322 | A | | 4/1928 | Itjen |
| 3,506,012 | A | | 4/1970 | Brown |
| 3,874,388 | A | | 4/1975 | King et al. |
| 4,394,864 | A | | 7/1983 | Sandhaus |
| 4,817,600 | A | | 4/1989 | Herms et al. |
| 4,944,741 | A | | 7/1990 | Hasson |
| 5,049,153 | A | | 9/1991 | Nakao et al. |
| 5,133,721 | A | | 7/1992 | Angulo |
| 5,172,700 | A | * | 12/1992 | Bencini et al. ............. 600/564 |
| 5,209,747 | A | | 5/1993 | Knoepfler |
| 5,217,484 | A | * | 6/1993 | Marks .................... 606/200 |
| 5,261,916 | A | * | 11/1993 | Engelson .................. 606/108 |

(Continued)

FOREIGN PATENT DOCUMENTS

DE    709 732    8/1941

OTHER PUBLICATIONS

Stöckel, (2000), "Nitinol Medical Devices and Implants," SMST-2000: Proceedings of the International Conference on Shape Memory and Suerelastic Technologies, 531-540.

(Continued)

*Primary Examiner*—Michael J. Hayes
*Assistant Examiner*—Michael G. Mendoza
(74) *Attorney, Agent, or Firm*—Kirkpatrick & Lockhart Preston Gates Ellis LLP (57) ABSTRACT

A coupling system is disposed at the distal end of an interventional delivery system for coupling to an implant. The coupling device has a first and second prong connected at one end. The other end of the prongs open or close to release or trap an object, e.g., a bead tethered from an implant. A slot at the distal end of the coupling device allows extra degrees of flexibility for the coupling device.

38 Claims, 7 Drawing Sheets

U.S. PATENT DOCUMENTS

| | | | |
|---|---|---|---|
| 5,281,230 A | 1/1994 | Heidmueller | |
| 5,282,826 A | 2/1994 | Quadri | |
| 5,304,185 A | 4/1994 | Taylor | |
| 5,338,317 A | 8/1994 | Hasson et al. | |
| 5,380,338 A | 1/1995 | Christian | |
| 5,383,888 A | 1/1995 | Zvenyatsky et al. | |
| 5,407,243 A | 4/1995 | Riemann | |
| 5,411,519 A | 5/1995 | Tovey et al. | |
| 5,413,583 A | 5/1995 | Wohlers | |
| 5,425,744 A | 6/1995 | Fagan et al. | |
| 5,464,408 A | 11/1995 | Due | |
| 5,486,185 A | 1/1996 | Freitas et al. | |
| 5,601,575 A | 2/1997 | Measamer et al. | |
| 5,601,595 A | 2/1997 | Smith | |
| 5,609,608 A | 3/1997 | Benett et al. | |
| 5,702,421 A | 12/1997 | Schneidt | |
| 5,713,908 A | 2/1998 | Jameel et al. | |
| 5,725,552 A | 3/1998 | Kotula et al. | |
| 5,752,973 A | 5/1998 | Kieturakis | |
| 5,797,939 A | 8/1998 | Yoon | |
| 5,797,959 A | 8/1998 | Castro et al. | |
| 5,800,457 A | 9/1998 | Gelbfish | |
| 5,810,864 A | 9/1998 | Schaller | |
| 5,853,420 A | 12/1998 | Chevillon et al. | |
| 5,867,877 A * | 2/1999 | Patterson et al. | 24/598.5 |
| 5,891,130 A | 4/1999 | Palermo et al. | |
| 5,951,564 A | 9/1999 | Schroder et al. | |
| 5,951,587 A | 9/1999 | Qureshi et al. | |
| 6,059,825 A | 5/2000 | Hobbs et al. | |
| 6,083,150 A * | 7/2000 | Aznoian et al. | 600/564 |
| 6,099,549 A | 8/2000 | Bosma et al. | |
| 6,171,329 B1 | 1/2001 | Shaw et al. | |
| 6,174,322 B1 | 1/2001 | Schneidt | |
| 6,206,907 B1 | 3/2001 | Marino et al. | 606/215 |
| 6,238,415 B1 * | 5/2001 | Sepetka et al. | 606/213 |
| 6,296,622 B1 * | 10/2001 | Kurz et al. | 604/93.01 |
| 6,364,846 B1 | 4/2002 | Nakamura | 600/564 |
| 6,379,368 B1 | 4/2002 | Corcoran et al. | 606/153 |
| 6,402,773 B1 | 6/2002 | Ouchi | 606/205 |
| 6,443,909 B1 | 9/2002 | Ouchi | 600/562 |
| 6,527,786 B1 | 3/2003 | Davis et al. | 606/151 |
| 6,544,274 B2 | 4/2003 | Danitz et al. | 606/157 |
| 6,582,450 B2 | 6/2003 | Ouchi | 606/205 |
| RE38,335 E | 11/2003 | Aust et al. | 606/170 |
| 6,666,876 B2 | 12/2003 | Kawai et al. | 606/205 |
| 6,685,724 B1 | 2/2004 | Haluck | 606/207 |
| 6,746,471 B2 | 6/2004 | Mortier et al. | 606/207 |
| 6,773,439 B2 | 8/2004 | George et al. | 606/141 |
| 6,800,085 B2 * | 10/2004 | Selmon et al. | 606/198 |
| 6,802,848 B2 | 10/2004 | Anderson et al. | 606/157 |
| 6,991,634 B2 | 1/2006 | Sugiyama et al. | 606/142 |
| 2002/0188316 A1 | 12/2002 | Dingler | 606/205 |
| 2003/0167055 A1 | 9/2003 | Kolata et al. | 606/1 |
| 2003/0181937 A1 | 9/2003 | Osterlind | 606/190 |
| 2003/0191494 A1 | 10/2003 | Gray et al. | 606/205 |
| 2003/0212435 A1 | 11/2003 | Gold et al. | 606/206 |
| 2004/0138701 A1 | 7/2004 | Haluck | 606/205 |
| 2004/0194264 A1 | 10/2004 | Johansson | 24/602 |

OTHER PUBLICATIONS

Latson, (1993), "Transcatheter Closure of Atrial Septal Defects," *Transcatheter Therapy in Pediatric Cardiology*, pp. 335-348.

* cited by examiner

COUPLING SYSTEM USEFUL IN PLACEMENT OF IMPLANTS

CROSS REFERENCE TO RELATED APPLICATIONS

This application claims priority to and the benefit of U.S. provisional patent application Nos. 60/364,017, filed Mar. 15, 2002, and No. 60/382,528, filed May 21, 2002. The disclosure of the above applications are hereby incorporated by reference.

TECHNICAL FIELD

The invention generally involves coupling or attaching devices used in a transcatheter delivery system and their uses in connection with delivering or retrieving a medical implant.

BACKGROUND OF THE INVENTION

Numerous systems for percutaneous transcatheter delivery of implants have been devised over the years in order to assist physicians in delivering and positioning implants, for example, occluders, within a patient, preferably in a minimally invasive manner. A problem with many of the known delivery systems is that they can often adversely affect positioning of the device that is being implanted, which forces the doctor to estimate and take into consideration such effect when assessing the final implant position prior to releasing the implant.

For example, most of the delivery systems include an elongated catheter that is used to access various passageways inside a patient's body. Often the desired position of the implant may not align with the longitudinal axis of the catheter. If the juncture between the implant and the catheter lacks sufficient flexibility, tension and torque will be generated at the juncture when the implant has to be bent off the catheter's axis in order to assume the desired position. Upon release of the implant, the tension and torque will affect both the implant and the delivery catheter, causing shifting in the implant position, and possible trauma to the surrounding tissue as the distal end of the catheter springs back to a more relaxed state. Such shifting in the implant position may result in a less desirable medical result (such as device embolization or a residual leak in the case of septal occluders).

Implants may include devices designed for compression into a small size tube or catheter to facilitate their introduction into the vasculature of the patient. The implants are subsequently expandable either to occlude defects or holes in the heart, in the case of septal occluders, or to contact the walls of the passageway (e.g., blood vessels), in the case of vena cava filters or stents. Among these devices are septal occluders well-known in the art such as the occluder described in U.S. Pat. No. 5,425,744 issued to Fagan et al. Septal occluders are useful in treating medical conditions such as patent foramen ovale (PFO), which is a persistent, one-way, often flap-like opening in the wall between the right atrium and left atrium of the heart, as well as other congenital and acquired defects in the heart or vasculature.

Presently, ball-to-ball (or pin-to-pin) attach/release mechanisms, such as the attach/release mechanism illustrated in *Transcatheter Therapy in Pediatric Cardiology* (1993): 335-348, have been employed by one skilled in the art to implant and position such septal occluders within the heart. The pin-to-pin mechanism illustrates the adverse effect the attachment juncture may cause in the positioning of the implant. With pin-to-pin mechanisms, the implant, a septal occluder, for example, is held nearly perpendicular to the longitudinal axis of a sleeve on the distal end of the delivery catheter. Due to the acute angle of delivery of the septal occluder from the inferior vena cava to the septal wall, the rigid pin-to-pin connection applies tension to the implant and the underlying septum, and compromises precise assessment of the final implant position prior to release of the implant.

Other types of attachment mechanisms known in the art include threaded male and female members as described in U.S. Pat. No. 5,725,552 issued to Kotula et al. This system, however, requires axial rotation of the members with respect to each other to disconnect the delivery device and also provides little flexibility, if any, for the lateral pivoting of the implant at the point it is attached to the delivery device.

Accordingly, there is a need for an interventional delivery system that allows assessment of proper positioning of an implant prior to release by the catheter.

SUMMARY OF THE INVENTION

The present invention provides novel and improved coupling systems and related methods, which may be useful for delivering, repositioning, and removal of an implant, such as a septal occluder, into and out of a patient.

The invention relates to a coupling device that allows pivoting of the implant at or near the juncture where the implant couples with the distal end of a delivery catheter, which is the coupling device. Specifically, the juncture is designed with a slot, for example, in the shape of a half-circle arc, that allows implant pivoting in a plane along the longitudinal axis of the coupling device. That feature, plus a trapping mechanism that allows implant rotation about the longitudinal axis of the coupling device, provides the much needed flexibility to avoid generating the tension that would otherwise cause bending at the coupling juncture and resulting in distortion of the underlying septum. Accordingly, after being released, the implant will stay where it was intended and the newly freed distal end of the delivery system will have less tendency to spring back and cause trauma to the surrounding tissue.

According to one aspect of the invention, a coupling or attachment device with a distal end is provided. The coupling device has an assembly that includes at least two prongs. Each of the prongs has a first and a second end. The prongs are connected at their first ends and free at their second ends. The second end of at least one of the prongs is movable from two positions: in an open position, the second ends of the two prongs are apart from each other; in a closed position, the second ends of the prongs are closer to each other than in the open position. Also in the closed position, the second ends of the two prongs define a slot at the distal end of the coupling device. The slot may be used for coupling an object to the coupling device, and is part of the solution to provide more flexibility at the coupling juncture. In one embodiment, the slot is an arc that spans about 180 degrees.

According to another aspect, the second end of only one prong is moveable. The other prong is fixed relative to the longitudinal axis of the coupling device.

According to yet another aspect of the invention, either the coupling device or the implant contains at least a portion that is magnetic. In one embodiment, at least a portion of at least one of the prongs is magnetic.

In one embodiment of the invention, at least one of the prongs is spring-biased. In one embodiment, the coupling device further includes a sleeve that moves relative to the prongs. The sleeve forces the prongs towards the closed position when the sleeve slides over at least a portion of the prongs. The prongs open into the open position when extended from the sleeve.

In another embodiment, at least one of the prongs has a recess, cavity, socket, concavity, cup, dent, or hole for receiving and trapping at least an object, such as a portion of an implant. The cavity may conform to the shape of the object such that when the object is trapped inside the cavity, the object is able to rotate about its own axis.

According to yet another aspect of the invention, the coupling device of the invention is assembled into an interventional delivery system that delivers an implant into a patient. The delivery system has a tubular portion with a lumen, and a core wire that slides inside the lumen of the tubular portion. The coupling device is disposed at the distal end of the core wire and is coupled to an implant.

In one embodiment, the implant has a tip that is spherical, and it fits a spherical cavity in the coupling device when the prongs of the coupling device are at the closed position. In one embodiment, the implant is a septal occluder. In another embodiment, the implant is an atrial appendage occlusion device or prosthesis.

A method for coupling an object is also provided herein to practice the invention. A coupling device according to the invention is provided. An object is coupled to the device when at least a tip of the object is trapped inside a cavity in the coupling device. The object may be allowed to pivot in the slot at the distal end of the coupling device.

BRIEF DESCRIPTION OF THE DRAWINGS

In the drawings, like reference numbers generally refer to the same parts throughout the different views. Also, the drawings are not necessarily to scale, emphasis instead generally being placed upon illustrating the principles of the invention.

DETAILED DESCRIPTION OF THE PRESENT INVENTION

An interventional delivery system described herein includes a tubular portion, a core wire that slides in the lumen of the tubular portion, and a coupling device at the distal end of the core wire that couples to an implant.

Figure 1:
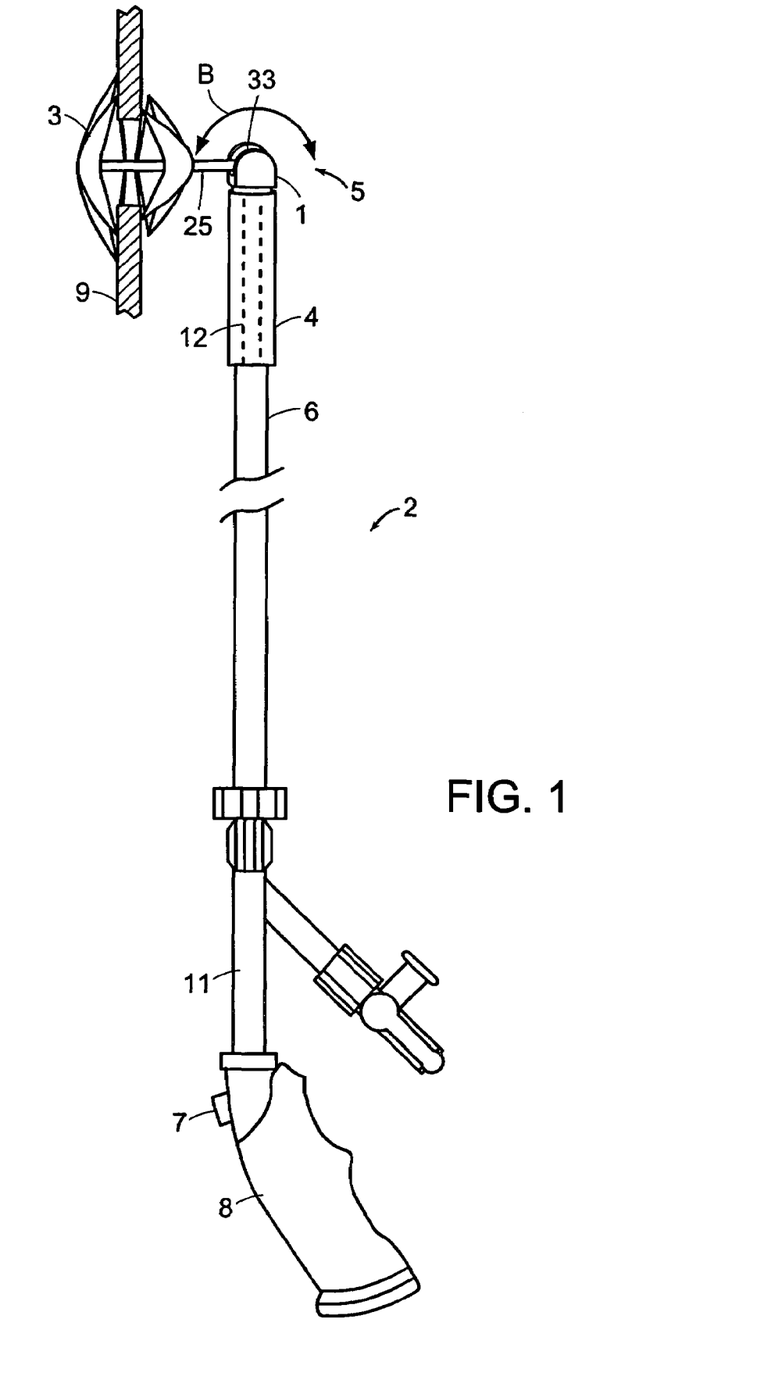
FIG. 1 is a plan view of an embodiment of an interventional delivery system with an implant linked to a coupling device disposed at the distal end of the interventional delivery system.

Referring to FIG. 1, in accordance with the present invention, a coupling device 1 disposed at the distal end 5 of an interventional delivery system 2 provides a mechanism for pivoting an implant 3 (e.g., a septal occluder) with respect to the coupling device 1 in order to avoid bending or twisting of the distal end 5 of the delivery system 2 during the delivery of the implant 3. In one embodiment according to the invention, the interventional delivery system 2 may include a distal sleeve 4 connected to a tubular body portion 6, which can be a catheter having a proximal end 11 connected to a handle 8. As an example, the implant 3 is shown to be a septal occluder planted in an opening in the atrial septum 9.

The term "implant" used herein includes devices, carriers, and objects that are placed in the body of a patient by invasive or minimally invasive methods, including but not limited to, prosthetic occluders, stents, filters, prostheses, valves, pumps, pace-makers, medications and so on. The implant may be permanent, semi-permanent, or temporary. The implant may be biodegradable. The implant may be removable through an interventional procedure. The implant may be a drug delivery device, such as capsules, tablets, or suppositories, for example, those that deliver pharmaceutical agents to the patient. In particular, the term implant includes intracardiac prosthetic occluders, for example, a septal occluder for the closing of, for example, patent foramen ovale, and an atrial appendage occlusion device or prosthesis.

With reference to FIGS. 2A-2D, in one embodiment according to the invention, the distal end 5 of the interventional delivery system 2 includes a distal sleeve 4. Inside the lumen 10 of the distal sleeve 4, a core wire 12 is able to slide relative to the distal sleeve 4. The sliding of the core wire 12 can be controlled through the handle 8 (FIG. 1). A coupling/gripping device 1 is secured to the distal end 14 of the core wire 12. There are a variety of ways to secure the coupling device 1 to the core wire 12, e.g., by extrusion, welding, soldering, molding, threading or by an adhesive. Being secured to core wire 12 enables the coupling device 1 and the distal sleeve 4 to move relative to one another. The sleeve 4 may be further enclosed in a catheter.

The coupling device 1 includes an assembly of two or more prongs. In this embodiment, two gripping prongs 15 and 15', each resembling a lobster claw, are positioned opposite each other. Prongs 15 and 15' each has a distal end 16, 16' respectively, and a proximal end 17, 17' respectively.

The prongs 15 and 15' are connected like pincers by a pin or pivot 18, at their proximal ends 17, 17', and are free, i.e., not connected at the distal ends 16, 16'. As a result, when the distal ends 16 and 16' are apart, the coupling device 1 is at an open position (e.g., FIG. 2A). In contrast, when the distal ends 16 and 16' are closer to each other, the coupling device 1 is at a closed position (e.g. FIG. 2D). In one embodiment of the invention, both prongs 15 and 15' pivot or turn about the pivot 18. In the embodiment shown in FIGS. 2A-2D, however, only one prong 15 is movable; the other prong 15' is fixed to the distal end 14 of the core wire 12 and does not pivot or articulate relative to the longitudinal axis of the core wire 12. Making only one prong moveable or pivotable relative to the core wire 12 decreases the cost of manufacture and lengthens the life span of the coupling device 1 because chances for mechanical misalignment are substantially reduced when the prongs 15, 15' close upon being retracted into the distal sleeve 4.

Figure 2A:
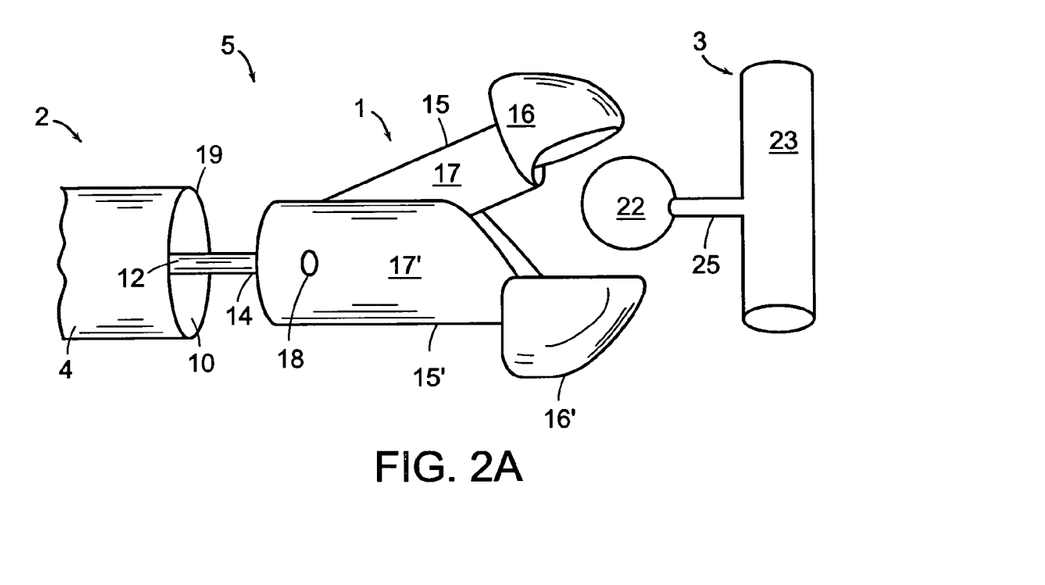
FIG. 2A is a perspective view of the distal end of an interventional delivery system including a coupling device in an open position in accordance with an embodiment of the present invention.
Figure 2B:
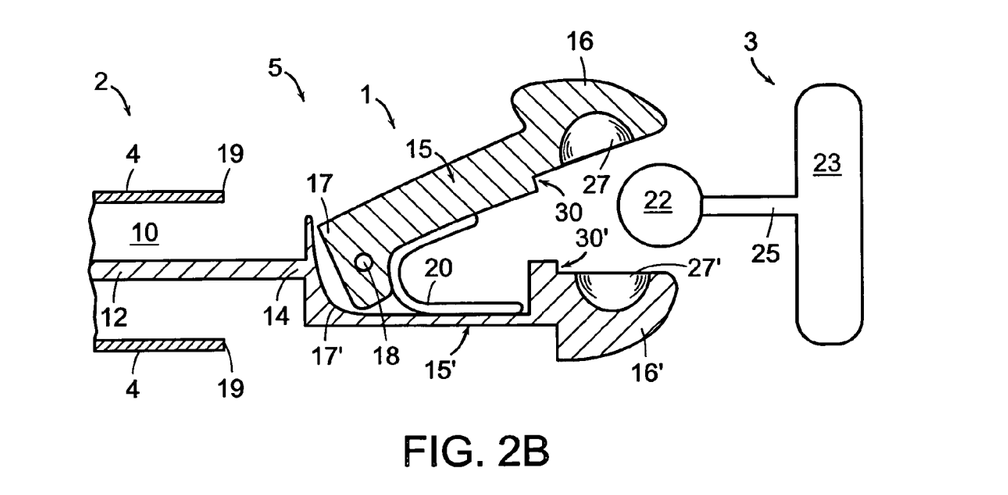
FIG. 2B illustrates a longitudinal cross-section of the embodiment of the distal end of an interventional delivery system illustrated in FIG. 2A.
Figure 2C:
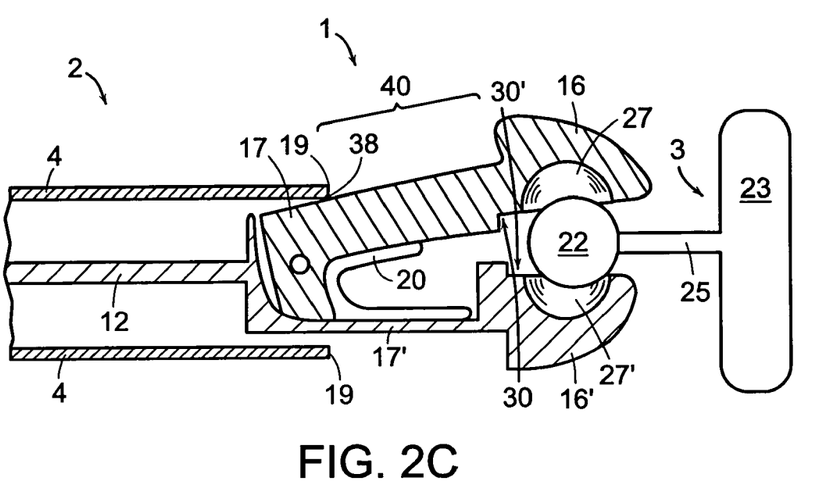
FIGS. 2C and 2D illustrate the embodiment shown in FIGS. 2A and 2B transition into a closed position to capture an implant.
Figure 2D:
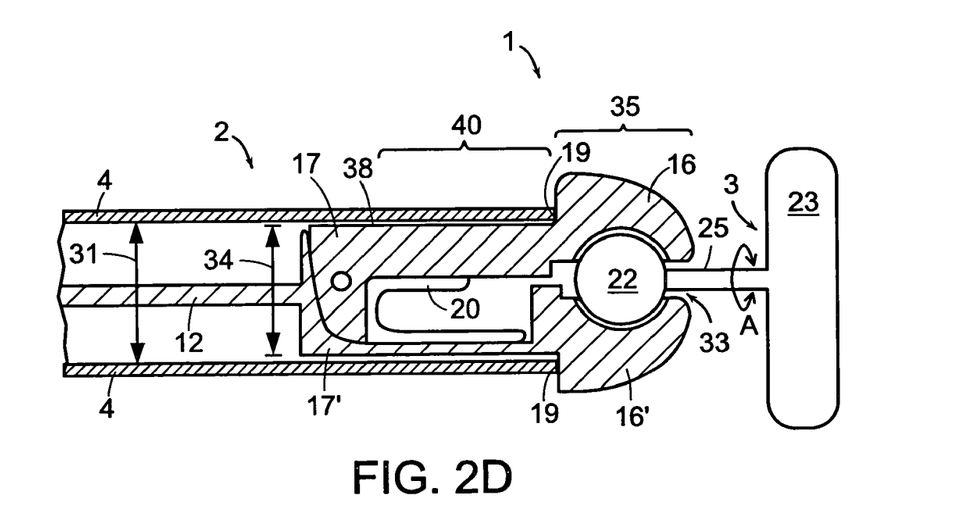

Referring to FIGS. 2B-2D, a spring member 20, e.g., a V-shaped wire, is disposed between the prongs 15 and 15', and biased to force the prong 15 outward towards the open position. The spring member 20 may be integrated into at least one of the prongs or may remain as a separate component. The spring member 20 can be manufactured from any suitable materials, e.g., stainless steel or nitinol.

Referring now to FIGS. 2A and 2B, the distal sleeve 4 is sized and shaped to slide over or enclose the prongs 15, 15'. When the prongs 15, 15' are extended entirely outside the distal sleeve 4, the coupling device 1 is in the open position (FIG. 2B). The distal end 16 of the first prong 15 is apart from the distal end 16' of the second prong 15' such that an intended target object is not secured by the coupling device 1. The target object can be of a variety of shapes, such as cubes, cylinders, cones, spheres, and so on. One embodiment of a target object is a spherical bead 22 linked to a main body 23 of the implant 3 through a tether 25. The tether 25 may be a wire, a thread, a strut, a tie with no particular limitation on its flexibility.

Figure 3A:
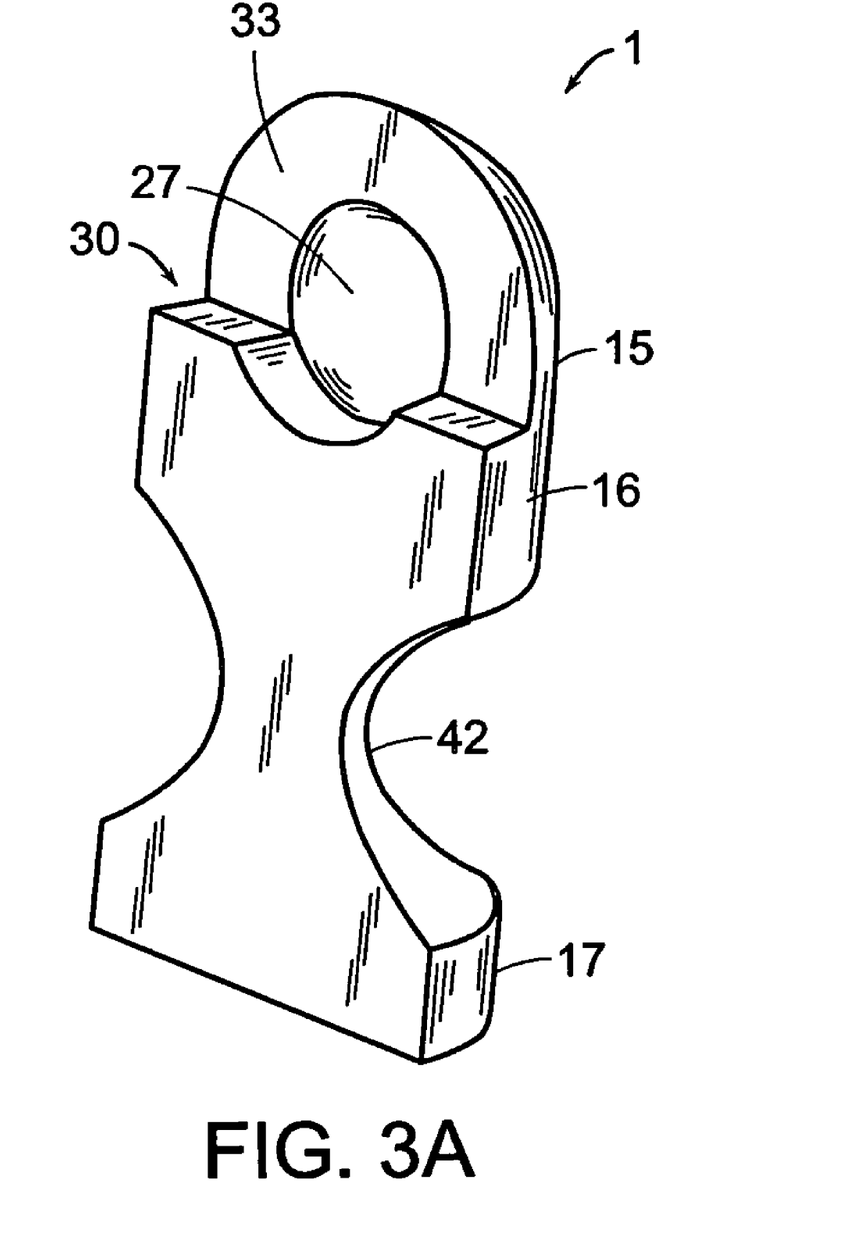
FIG. 3A is a perspective view of a portion of another embodiment of a coupling device according to the invention.

Referring now to FIG. 3A, at least one of the prongs, for example, prong 15 of the coupling device 1 has a cavity 27 to grip and trap the target object. Further, there may be cavities 27, 27' in the distal ends 16, 16' of both the prongs 15 and 15' as shown, for example, in FIG. 2B. Cavities 27, 27' are preferably shaped to conform to the shape of the target object, e.g., the bead 22 of the implant 3. In other words, both cavities 27 and 27' are substantially a halfspherical concavity and together form a spherical concavity. Referring now to FIG. 2D, cavities 27, 27' may also be sized to allow the implant 3 to rotate about the tether 25 as shown by arrows "A" when the prongs 15 and 15' are in the closed position.

Figure 3B:
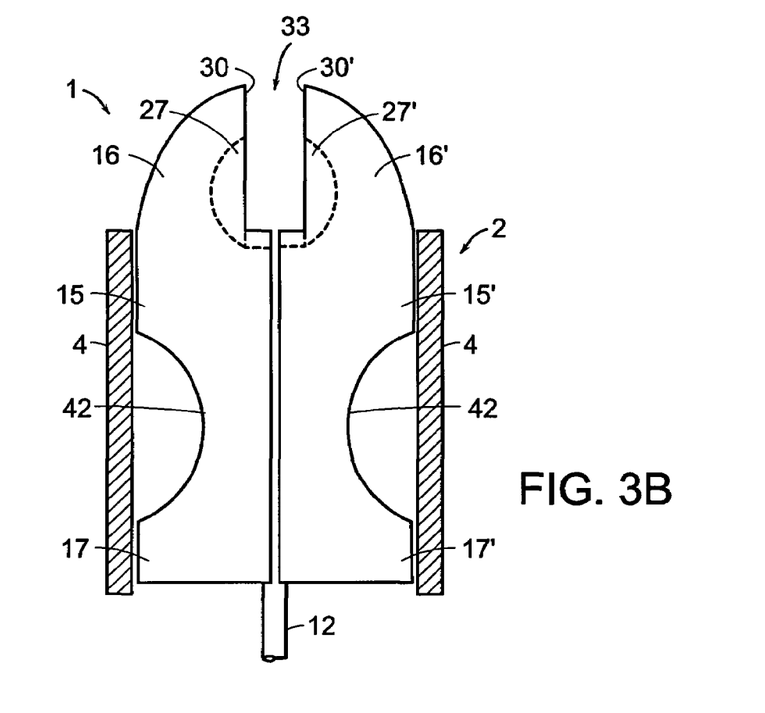
FIG. 3B is a partial cross-sectional view of an embodiment of a coupling device according to the invention.
Figure 3C:
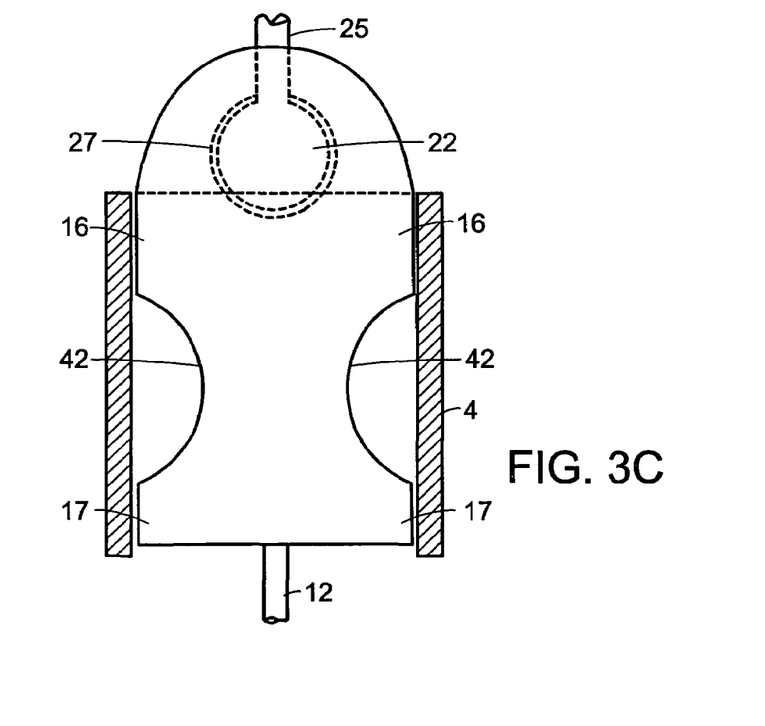
FIG. 3C is a partial cross-sectional view of the embodiment of FIG. 3B rotated 90° and with part of an implant trapped therein.
Figure 3D:
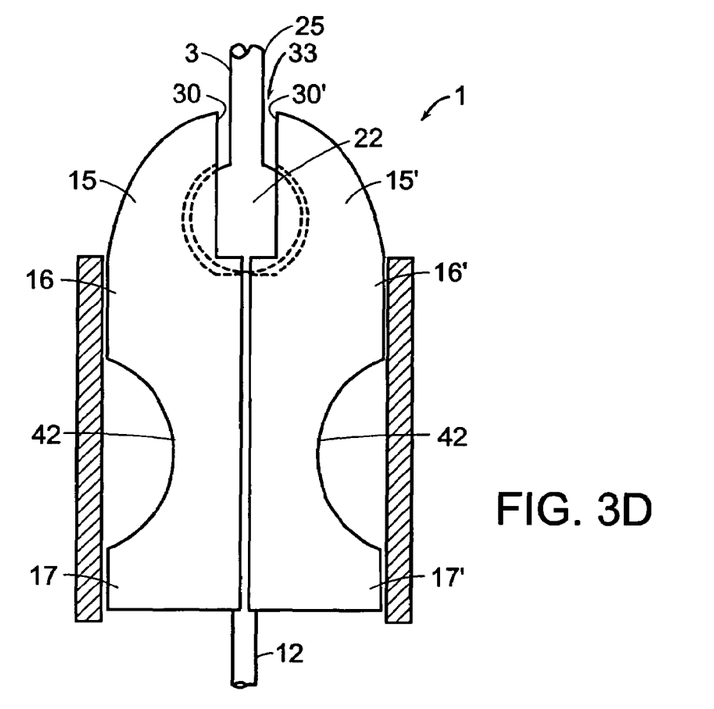
FIG. 3D is a partial cross-sectional view of the embodiment of FIG. 3B device with part of an implant trapped therein.

Referring to FIGS. 2B, 2C and 3A, each of the prongs 15 and 15' may also include recesses 30 and 30' adjacent the cavities 27 and 27' respectively. Referring to FIG. 3B, the recesses 30 and 30' together form a slot 33 between the prongs 15 and 15' when the prongs 15 and 15' are in the closed position. The slot 33 may be an arc spanning between 0 to 360°, e.g., about 90° or 270°, or 180° as illustrated in FIGS. 3A and 3B. Referring to FIGS. 2D, 3C, and 3D, the slot 33 is sized to fit the tether 25 that links the trapped bead 22 to the main body 23 of the implant 3. Referring again to FIG. 1, when the prongs 15 and 15' are in the closed position and the bead 22 is trapped by the cavities 27 and 27', the tether 25 may pivot in the slot 33 in an arc indicated by arrows "B," providing the implant 3 with the crucial ability to pivot at the coupling juncture without causing undesired tension to the distal end 5 of the interventional delivery system 2. The slot 33 and the cavities 27, 27', which provide axial rotation for the implant 3, together enable a medical personnel to position the implant 3 in a variety of orientations without having to bend the delivery catheter.

Referring back to FIG. 2D, in one embodiment according to the invention, the distal ends 16, 16' of the prongs 15 and 15', may have a larger outer diameter than the proximal ends 17, 17', creating a cap 35 or a mushroom head. In the closed position illustrated, e.g., in FIG. 2D, the outer diameter of the combined distal ends 16, 16', is larger than the lumenal diameter 31 of the distal sleeve 4. And the lumenal diameter 31 of the distal sleeve 4 is larger than the outer diameter 34 of the proximal ends 17, 17' combined and measured at the closed position. As a result, the distal sleeve 4 is slideably moveable over the proximal ends 17, 17' as shown in FIG. 2C, but the distal rim 19 of the distal sleeve 4 will stop when the rim 19 abuts the cap 35, as shown in FIG. 2D. The mushroom head shape sets a limit to the relative positions between the distal sleeve 4 and the coupling device 1, and can assist an operator in determining the precise length of sliding required of the distal sleeve 4 to release the captured implant 3.

Referring again to FIGS. 2A-2D, when the distal sleeve 4 moves distally towards the coupling device 1, the distal rim 19 of the distal sleeve 4 hits the moveable prong 15, and starts to force the prong 15 to move from the open position illustrated in FIG. 2A to the closed position illustrated in FIG. 2D. The space between the cavities 27 and 27' also starts to decrease. FIG. 2C illustrates the "pivot point" 38 on the moveable prong 15. A pivot point is the point on the outer wall of the prongs 15, 15' that, when the distal rim 19 of the distal sleeve 4 advances to it, the space between the cavities 27 and 27' has decreased such that the bead 22, if captured, can no longer exit the cavities 27 and 27'. Referring to FIGS. 2C and 2D, when the distal rim 19 of the distal sleeve 4 is positioned between the pivot point 38 on the proximal portion 17 and the cap 35, the implant is reversibly secured or coupled to the coupling device 1. The distance between the pivot point 38 and the cap 35 where the distal sleeve 4 cannot advance any further, is called the "float range" 40.

In a particular embodiment, the "float range" 40 is maximized, e.g., to substantially equal the entire length of the proximal ends 17, 17' by positioning the pivot point 38 as proximal on the proximal ends 17, 17' as possible. Referring to FIG. 2D, this may be achieved by minimizing the clearance between the inner wall of the distal sleeve 4 and the outer wall of the proximal ends 17, 17' of the coupling device 1 when the device 1 is in the closed position. In other words, there can be provided a distal sleeve 4 whose lumenal diameter 31 is as close as possible to the outer diameter 34 of the proximal ends 17, 17' of the coupling device 1 at the closed position. In a particular embodiment, the lumenal diameter 31 and the outer diameter 34 are substantially the same. As long as the distal rim 19 of the distal sleeve 4 is within the "float range" 40, the bead 22 of the implant 3 will be trapped inside the cavities 27 and 27' of the coupling device 1, minimizing inadvertent release of the implant 3.

Figure 3E:
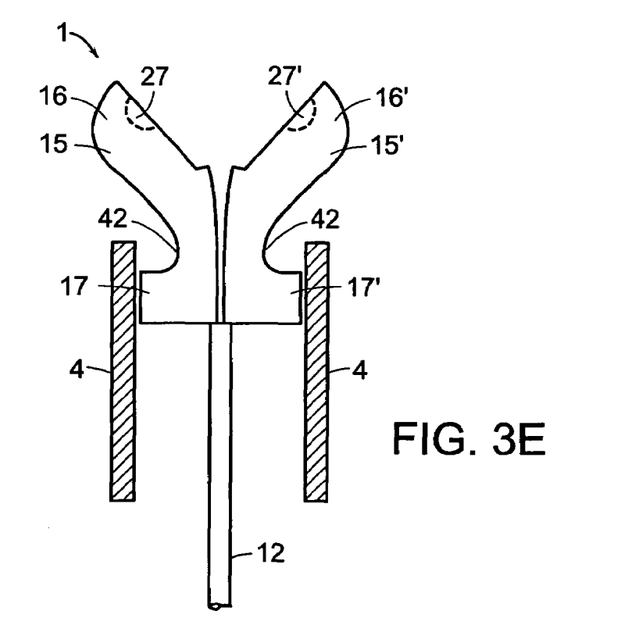
FIG. 3E is a partial cross-sectional view of the embodiment of FIG. 3B in an open position.

The material for the prongs 15, 15' may include but is not limited to stainless steel, titanium, nitinol, etc. One embodiment of the invention takes advantage of the elasticity in the material, such as nitinol, used for the prongs 15, 15'. Referring to FIG. 3A, at least one of the prongs, e.g., the prong 15, may include a portion 42 that is reduced in width for extra flexibility between the distal end 16 and the proximal end 17. Referring to 3E, because the elasticity in the material for the prongs 15, 15', the distal ends 16, 16' will bend or pivot with respect to the proximal ends 17, 17' respectively. Accordingly, when the distal ends 16, 16' are outside the distal sleeve 4, the distal ends 16, 16' will bend away from each other into the open position. In this embodiment, there is no need for a spring member in between the prongs 15, 15' in order to achieve the open position.

Figure 4A:
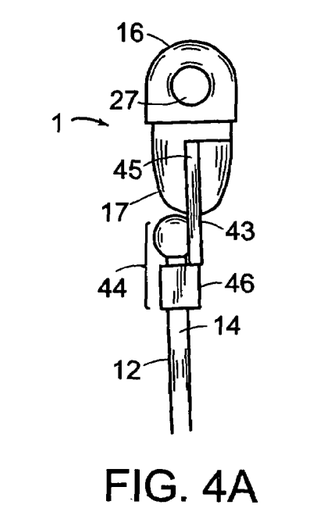
FIGS. 4A-4C are perspective views at various angles of an embodiment according to the invention.
Figure 4B:
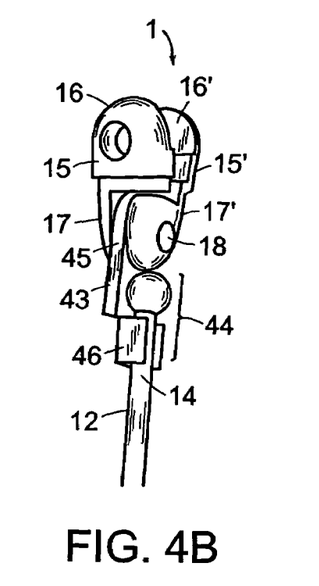
Figure 4C:
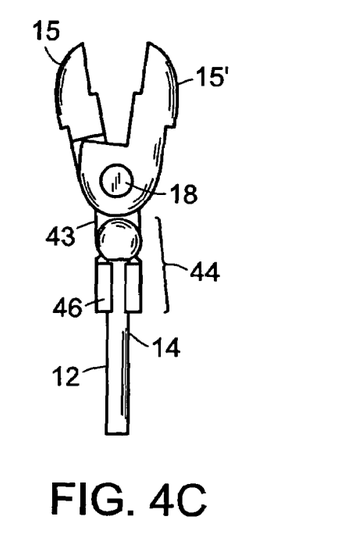
Figure 4D:
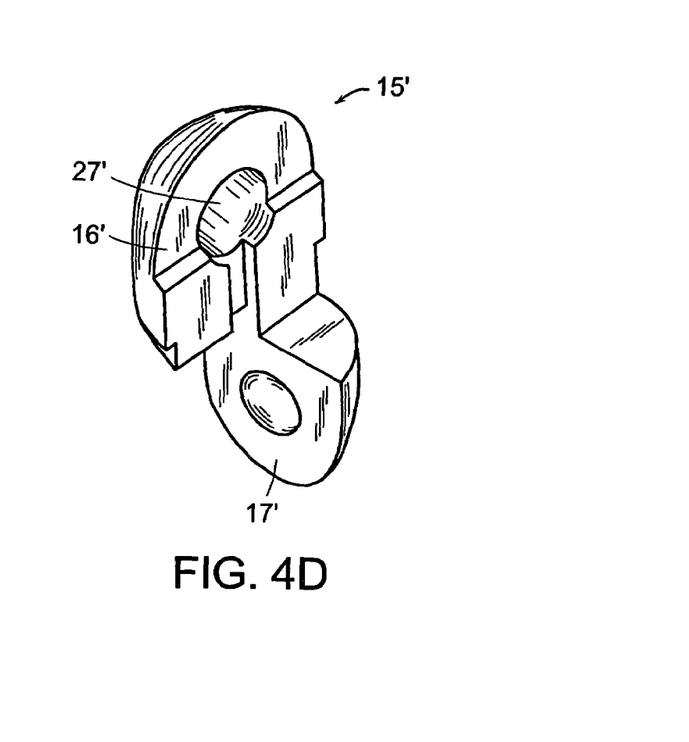
FIG. 4D is a perspective view of a portion of the embodiment shown in FIGS. 4A-4C.

In the exemplary embodiment shown in FIGS. 2A-2D, one of the prongs 15' is longer than the other prong 15, and the proximal end 17' of the prong 15' is fixedly secured to the distal end of the core wire 12. The proximal end 17 of the other prong 15 is pivotly joined, by a pin 18, to the proximal end 17' of the longer prong 15'. Therefore, the opening and closing of the coupling device 1, in this embodiment, depends on the movement of the prong 15. In another embodiment shown in FIGS. 4A-4C, the proximal end 17' of the prong 15' is not fixedly secured to the core wire 12, but pinned together with a distal end 45 of a connector piece 43 and the proximal end 17 of the prong 15, all though the pin 18. The proximal end 46 of the connector piece 43 is, in turn, connected to the distal end 14 of the core wire 12 through, e.g., a ball-and-socket joint 44. A more detailed view of one of the prongs, e.g., the prong 15', is provided in FIG. 4D.

Referring back to FIG. 2A, in another aspect of the invention, either the coupling device 1 or the implant 3 contains at least a portion that is magnetic. For example, the prongs 15 and 15' can be magnetic, and the implant bead 22 may be ferromagnetic. Such magnetic properties make it easier to capture or recapture the bead 22, which can be very small.

The present system contemplates a coupling system between the catheter and implant, such as a septal occluder, which provides pivoting and axial rotation in order to minimize forces exerted on the device as well as the septum of the heart. The system may have more than two prongs in accordance with the invention. For example, a system with four prongs may have two slots forming a cross-like section that allows the trapped implant tip to move in two orthogonal planes defined by the slots.

The present invention also includes methods related to the systems described above including methods of using the system. Referring back to FIG. 1, once the prongs of the coupling device 1 have trapped part of the implant 3, and the coupling device 1 has been at least partially retracted into the distal sleeve 4, the doctor can extend the interventional delivery system 2 with its distal end 5 coupled to the implant 3 into a body lumen such as the vascular passageway. Once the distal end 5 of the delivery system 2 reaches the target region, e.g., an opening in the atrial septum 9, the implant 3, e.g., a septal occluder, may be rotated about the axis of the core wire 12 of the delivery system 2. Moreover, the doctor may pivot the implant 3 by its tether 25 with respect to the coupling device 1 along the slot 33 formed between the prongs of the coupling device 1 as indicated by the arrow "B". The rotation and pivoting action minimize forces acting on the coupling device 1 and the atrial septum 9 where the implant 3 is implanted.

Once the implant 3 is satisfactorily positioned within the cardiac chamber, the doctor may release the implant 3, e.g., by pushing an actuating button 7 on the handle 8 to advance the core wire 12 and the coupling device 1 out of the distal sleeve 4 into the open position. Conversely, when retrieving or repositioning the implant 3, the coupling device 1 would be actuated to the open positioned to capture the implant 3, e.g., by its tethered bead. Then, the coupling device 1 is at least partially retracted into the distal sleeve 4, forcing the prongs to collapse into the closed position and trapping the bead of the implant 3. As described above, magnetism in either or both the coupling device 1 and the implant 3 would aid the recapturing of the implant 3. After the implant 3 has been recaptured by the coupling device 1, the doctor may maneuver the interventional delivery system 2 to a desired location to reposition the implant 3 or out of the patient's body to remove the implant 3.

OTHER EMBODIMENTS

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for coupling an implant, the device comprising:
   a distal end;
   a pivot;
   a first prong and a second prong each comprising a first end and a second end, the first prong and second prong being connected by the pivot at their first ends and free at their second ends, each of said first and second prongs having an outer surface and an inner surface, the inner surface of at least one of the prongs comprising a recess, the inner surface of the second end of each prong comprising a cavity, the proximal end of the cavity terminating distal to the pivot, at least one of the first prong and the second prong being reversibly movable between an open position and a closed position; and
   the at least one recess forming a slot comprising a proximal end, a distal end, and an arc shape extending from the distal end of the device, the proximal end of the slot terminating distal to the pivot, the slot being defined by the second end of at least one of the prongs when the first prong and the second prong are in the closed position.

2. The device of claim 1 wherein at least one of the prongs is spring biased.

3. The device of claim 1 wherein the second end of only one prong is moveable.

4. The device of claim 1 further comprising a sleeve slideably moveable relative to the first and second prongs, the sleeve forcing the second end of at least one of the prongs toward the closed position when the sleeve slides over at least a portion of the prongs.

5. The device of claim 1 wherein the arc-shaped slot spans substantially 180 degrees.

6. The device of claim 1 wherein the cavity is shaped to conform to the shape of the implant wherein the implant is capable of rotating within the cavity.

7. The device of claim 1 wherein the cavity comprises at least a portion of a spherical concavity.

8. The device of claim 1 wherein an outer diameter of the second ends of the two prongs combined in the closed position is larger than an outer diameter of the first ends of the two prongs combined.

9. The device of claim 1 further comprising a sleeve slideably moveable relative to the prongs, the sleeve defining a lumen, wherein the prongs are in the closed position when the first ends of the prongs are enclosed in the lumen of the sleeve and the prongs are in the open position when the first ends of the prongs extend out of the lumen of the sleeve.

10. The device of claim 1 wherein the prongs further comprise a float range comprising substantially the entire length of the first ends of the prongs.

11. The device of claim 1 wherein at least a portion of at least one of the prongs is magnetic.

12. The device of claim 1 wherein the arc-shaped slot spans from about 90 to about 270 degrees.

13. The device of claim 1 further comprising a sleeve comprising an outer diameter, wherein the outer diameter of the sleeve is smaller than the outer diameter of the second end of the first prong and the second end of the second prong when the first prong and the second prong are together in the closed position.

14. The device of claim 1 wherein the pivot comprises a pin.

15. The device of claim 1 wherein the second end of the first prong and the second end of the second prong are maximally apart in the open position and the second end of the first prong and the second end of the second prong are maximally closer to each other in the closed position than in the open position.

16. The device of claim 1 wherein the recess is located at the second end of at least one of the first prong and the second prong.

17. An interventional delivery system for delivering an implant into a patient, comprising:
   a tubular portion defining a lumen;
   a core wire comprising a distal end and having a longitudinal axis, the core wire slideably moveable in the lumen of the tubular portion; and
   a coupling device at the distal end of the core wire, the coupling device comprising a distal end, a pivot, a first prong and a second prong each comprising a first end and a second end, the first prong and second prong being connected by the pivot at their first ends and free at their second ends, each of said first and second prongs having an outer surface and an inner surface, the inner surface of at least one of the prongs comprising a recess, the inner surface of the second end of each prong comprising a cavity, the proximal end of the cavity terminating distal to the pivot, and at least one of the first prong and the second prong being reversibly movable between an open position and a closed position, and the at least one recess forming a slot comprising a proximal end, a distal end, and an arc shape extending from the distal end of the device, the proximal end of the slot terminating distal to the pivot, the slot being defined by the second end of at least one of the prongs when the first prong and the second prong are in the closed position.

18. The system of claim 17 wherein the cavity comprises at least a portion of a spherical concavity.

19. The system of claim 17 further comprising a handle connected to the tubular portion, the handle comprising an actuator for actuating the core wire.

20. The system of claim 17 wherein at least one of the prongs is spring biased.

21. The system of claim 17 wherein the second end of only one prong is moveable.

22. The system of claim 17 further comprising a sleeve slideably moveable relative to the first and second prongs, the sleeve forcing the second end of at least one of the prongs toward the closed position when the sleeve slides over at least a portion of the prong.

23. The system of claim 17 wherein the arc-shaped slot spans substantially 180 degrees.

24. The system of claim 17 further comprising an implant.

25. The system of claim 24 wherein the implant comprises a tip and the cavity in each prong is shaped to conform to the shape of the implant tip wherein the implant tip is capable of rotating within the cavity.

26. The system of claim 24 wherein the implant comprises a spherical tip.

27. The system of claim 24 wherein the implant comprises a septal occluder.

28. The system of claim 24 wherein the implant comprises an atrial appendage occlusion device.

29. The system of claim 24 wherein at least a portion of the implant is magnetic.

30. The system of claim 17 wherein one of the prongs is fixedly connected to the distal end of the core wire.

31. The system of claim 17 wherein at least one prong is rotatably connected to the distal end of the core wire.

32. The system of claim 17 wherein at least a portion of at least one of the prongs is magnetic.

33. The system of claim 17 wherein the arc-shaped slot spans from about 90 to about 270 degrees.

34. The system of claim 17 further comprising a sleeve comprising an outer diameter, wherein the outer diameter of the sleeve is smaller than the outer diameter of the second end of the first prong and the second end of the second prong when the first prong and the second prong are together in the closed position.

35. The system of claim 17 wherein the pivot comprises a pin.

36. The system of claim 17 wherein the second end of the first prong and the second end of the second prong are maximally apart in the open position and the second end of the first prong and the second end of the second prong are maximally closer to each other in the closed position than in the open position.

37. The system of claim 17 wherein the recess is located at the second end of at least one of the first prong and the second prong.

38. A method for coupling an implant, the method comprising:
   providing a coupling device comprising a distal end, a pivot, a first prong and a second prong each comprising a first end and a second end, the first prong and second prong being connected by the pivot at their first ends and free at their second ends, each of said first and second prongs having an outer surface and an inner surface, the inner surface of at least one of the prongs comprising a recess, the inner surface of the second end of each prong comprising a cavity, the proximal end of the cavity terminating distal to the pivot, at least one of the first prong and the second prong being reversibly movable between an open position and a closed position, and a slot comprising a proximal end, a distal end, and an arc shape extending from the distal end of the device, the proximal end of the slot terminating distal to the pivot, the slot being defined by the second end of at least one of the prongs when the first prong and the second prong are in the closed position; and
   trapping at least a tip of an implant in the cavity in at least one of the prongs.

* * * * *